United States Patent [19]

Bailey et al.

[11] Patent Number: 5,656,265

[45] Date of Patent: Aug. 12, 1997

[54] HAIR STYLING COMPOSITION AND METHOD

[75] Inventors: Peter Lawrence Bailey, Wirral; Anthony David Gough, Oakley; Ezat Khoshdel, Neston; Robert Polywka, Guilden Sutton, all of United Kingdom

[73] Assignee: Chesebrough-Pond's USA Co., Division of Conopco, Inc., Greenwich, Conn.

[21] Appl. No.: 469,325

[22] Filed: Jun. 6, 1995

[30] Foreign Application Priority Data

Aug. 5, 1994 [GB] United Kingdom ............... 9415911

[51] Int. Cl.$^6$ .................. A61K 7/06; A61K 7/11
[52] U.S. Cl. ............ 424/70.1; 424/70.5; 132/202; 132/203
[58] Field of Search ............... 424/70.1, 70.11, 424/70.5; 132/202, 203

[56] References Cited

U.S. PATENT DOCUMENTS

| | | |
|---|---|---|
| 4,097,444 | 6/1978 | Teige et al. . |
| 4,867,966 | 9/1989 | Grollier et al. . |
| 4,981,933 | 1/1991 | Faxio et al. . |
| 5,013,795 | 5/1991 | Coleman et al. . |
| 5,200,471 | 4/1993 | Coleman et al. . |

FOREIGN PATENT DOCUMENTS

| | | |
|---|---|---|
| 0392735 | 10/1990 | European Pat. Off. . |
| 0443034 | 6/1991 | European Pat. Off. . |
| 0529437 | 3/1993 | European Pat. Off. . |
| 1212418 | 7/1968 | United Kingdom . |
| 1202119 | 8/1970 | United Kingdom . |
| 1469307 | 4/1977 | United Kingdom . |
| 1558847 | 1/1980 | United Kingdom . |
| WO94/26237 | 11/1994 | WIPO . |

OTHER PUBLICATIONS

J. Cosmet Chem, 1977, pp. 231–241.
International Search Report PCT/EP 95/02936.
Chemical Abstract 112:199261 (1990).
Chemical Abstract 87:117306 (1977).
Chemical Abstract 118:169689 (1993).

*Primary Examiner*—Sallie M. Gardner
*Attorney, Agent, or Firm*—Milton L. Honig

[57] ABSTRACT

A hair styling and conditioning process comprising the steps of: contacting the hair with a compound having an electrophilic group and at least one hydrophobic group whereby the electrophilic group reacts with nucleophilic sites in and on the hair to give the hair a plurality of hydrophobic groups at the surface, in which the hydrophobic group is selected from the group consisting of $C_{10-30}$ and $C_{10-30}$ alkenyl groups. Preferably the electrophilic group is azlactone.

Also a reversible hair styling process in which the hydrophobic group is selected from the group consisting of $C_{1-30}$ alkyl, $C_{2-30}$ alkenyl, phenyl, diphenyl, other aromatics, and fluoroalkanes, and the electrophilic group is selected from the group consisting of azlactone, sulphide from disulphide, sulphide from thiosulphonate, vinyl zulphone, vinyl sulphoximines, banzoxazinones and isocyanates.

Novel azlactones, including pentadecyl and hexyl azlactone.

7 Claims, No Drawings

HAIR STYLING COMPOSITION AND METHOD

This invention relates to compositions and methods for the styling of hair by chemical interaction of the compositions with at least one species of nucleophilic group in the hair.

Permanent waving of hair is well known and usually comprises reduction of disulphids groups with thioglycollate followed by realignment of sulphydryl groups then oxidation with peroxide to complete the process. A problem with such permanent styling is that it cannot be varied according to day to day wishes and it is a harsh process which damages the hair. Temporary styling takes the form of various sprays, mousses and gels which are applied to the hair after washing. These products are designed to be washed out and are not very durable in humid atmospheres. Furthermore, the products have unwelcome sensory negatives due to deposition of relatively large quantities of polymers and other synthetic materials on the hair. It is an object of the present invention to provide a permanent treatment of the hair which gives a style which can be repeatedly changed or even removed according to the wishes of the user. Thus the hair can be straight during the day and curly in the evening or for the weekend.

EP-A-0392735 (Minnesota Mining and Manufacturing Company), discloses azlactone-functional polymeric solid supports which are useful as complexing agents, catalysts, reagents, adsorbents, chromatographic supports and as biologically active supports for reaction with protein.

Reversible styling of hair is disclosed by K. E. Hall and L. J. Wolfram, J Cosmet Chem, 1977, 28, 231–241. They reduce the disulphide bonds within the hair fibre and reacted the newly formed sulphydryl groups with an alkyl halide or a maleimide.

This two step treatment has the effect of introducing hydrophobic groups within the fibre giving rise to an increase in the number of hydrophobic bonds present thus leading to retention of set. This technology suffers from safety considerations regarding the alkylation step and does not give sufficient style retention for modern requirements.

Copending International application number; EP/94/01476 describes a method of treating hair comprising taking an azlactone functionalised cosmetic agent and reacting it with a nucleophilic site on the hair to fix the cosmetic agent to the hair. In this application, polymer bearing azlactones are shown to covalently bind to hair. The reaction mechanism is thought to involve nucleophilic attack on the azlactone ring by nucleophilic species within the hair fibre. The cosmetic agents used are polymers which are conditioning agents or styling/bodying/setting agents. Materials suggested are silicone polymers, hydrocarbon polymers, perfluoro-aliphatic or -aromatic compounds, chitosan and chitosan-derivatives, cationic polymers, cationic derivatives of guar gum and cellulose ether derivatives, film-forming polymers, reactive derivatives of sunscreen materials, reactive dyes and colouring agents.

According to the present invention there is provided a hair styling and conditioning process comprising the snaps of: contacting the hair with a compound having an electrophilic group and an least one hydrophobic group whereby the electrophilic group reacts with nucleophilic sites on and in the hair to give the hair a plurality of hydrophobic groups characterised in that the hydrophobic group is selected from; $C_{10-30}$ alkyl and alkenyl groups.

The hydrophobic group may be branched or linear. To give a good conditioning benefit the hydrophobic group may be $C_{11}-C_{14}$ alkyl, preferably $C_{11}$ or $C_{15}$, most preferably $C_{15}$.

The invention also comprises a reversible hair styling process comprising the steps of: contacting the hair with a compound having an electrophilic group and at least one hydrophobic group whereby the electrophilic group reacts with nucleophilic sites on and in the hair to give the hair a plurality of hydrophobic groups characterised in that the hydrophobic group is selected from: $C_{1-30}$ alkyl or alkenyl, phenyl, diphenyl, and other aromatics (e.g. naphthyl), fluoroalkanes, and the electrophilic group is selected from the group comprising azlactone, sulphide from disulphide or thiosulphonate, vinyl sulphone, vinyl sulphoximines, isocyanates and benzoxazinones.

Preferably the electrophilic group is azlactone. This class of materials combine the advantageous properties of fast reaction time, good safety and system stability.

Advantageously the hair is contacted with a reducing agent before it is treated with the electrophilic group. This increases the number of reactive sites and promotes greater stylability and conditioning due to the larger number of hydrophobic groups attached to the hair.

The preferred reducing agent is a thioglycollate, most preferably ammonium thioglycollate.

The invention further comprises a process in which styled hair is restyled by contacting the styled hair with a liquid containing hydrophilic and hydrophobic groups then setting the hair. The ability to restyle the hair a number of times without the need to repeat the harsh thioglycollate treatment used in the perming process is very desirable, especially when the style is more resistant to moisture and humidity than a water wave.

The liquid conveniently contains alcohol such as propanol.

Also falling within the present invention are the novel azlactones: Pentadecyl azlactone, hexyl azlactone, Phenylalanine azlactone etc.

Azlactone Functionalised Styling Agent

The composition according to the invention may comprise at least one azlactone functionality chemically bonded to a hydrophobic group which can interact with similar hydrophobic groups on adjacent hairs for instance by forming hydrophobic bonds. By "azlactone" is meant the following group:

Formula 1

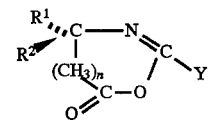

wherein $R^1$ and $R^2$ are the same or different and each is independantly selected from H, and $C_{1-14}$ alkyl groups, preferably lower ($C_1-C_4$) alkyl e.g. methyl; a $C_{2-14}$ cycloalkyl group; a $C_{5-12}$ aryl ring group; a $C_{6-24}$ arenyl group with up to 3 S, N or O heteroatoms; or $R^1$ and $R^3$ taken together with the carbon atom to which they are joined can form a carbocyclic ring containing 4 to 12 ring atoms, and n is an integer from 0 to about 12, preferably up to about 3, most preferably 0, Y is the hydrophobic group.

When the azlactone functionalised hydrophobic group is applied to the reduced hair in accordance with the invention, the azlactone group reacts with nucleophiles on the surface of the hairand within the hair, resulting in a ring-opening reaction represented by the following scheme for reduction with thioglycollate and acylation with an alkyl azlactone.

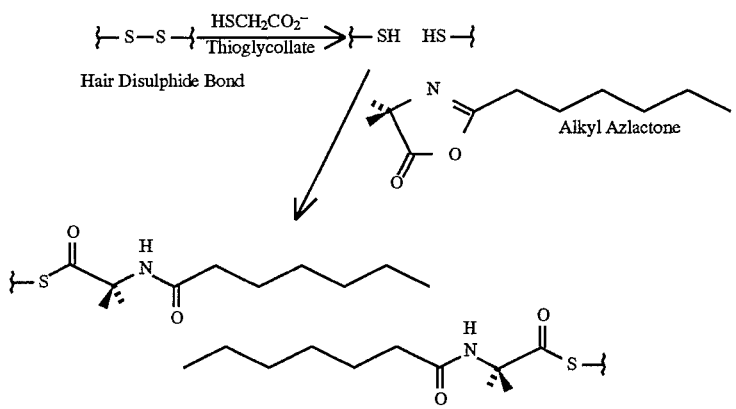

The azlactone materials may be prepared by conventional synthetic routes as are well known in the art. One particularly preferred family of reactive species (a) are alkyl groups especially $C_{15}$ alkyl groups. Aromatic groups may also be used such as diphenyl groups or other cyclic groups which can rotate.

Compositions Comprising the Azlactone Functionalised Hydrophobic Group

In this aspect of the present invention, a styling composition comprises at least one of the above described azlactone-functionalised hydrophobic groups, together with any additional ingredients which are normally to be found in treatment compositions for use on hair. One or more of the azlactone styling agents may be used.

Whilst aqueous or aqueous/alcoholic solution based compositions, or possibly organic solvent-based compositions, in which the one or more azlactone functionalised agents are dissolved are preferred, the composition may comprise stable emulsions of the azlactone which are water-insoluble.

We have found that the pH of the compositions of the invention is relevant to achieving optimised chemisorption of the functionalised agent on the hair. Chemisorption occure in a range of pH from 3–9.

The styling compositions according to the invention may be provided in any suitable physical form, for example as low to moderate viscosity liquids, lotions, milks, mousses, sprays, gels and creams.

It is preferable for the styling process to include a retention step during which the composition containing the active is left in contact with the hair for a period of time sufficient for the azlactone rings to react with the nucleophilic site on the hair substrate surface.

The invention will now be further illustrated by way of the following non-limiting examples, Preparation of the Azlactones Hydrophobically modified azlactones are prepared via the synthesis of the appropriate N-Acyl Aminoacid. These amino acids may be prepared by following this general procedure.

In a suitable flange pot equipped with overhead stirrer, thermometer and dropping funnel, sodium hydroxide (1 mol) is dissolved in water (375 ml) where the acid chloride is heptanoyl or palmitoyl chloride the water is replaced with acetone/water 3:1. The pot temperature is reduced to approx 10° C. and the amino acid (0.5 mol) is added in portions— maintaining the temperature at 10°/15° C. Upon completion of the addition the reaction mixture is stirred until complete dissolution has been achieved. The desired acid chloride (0.5 mol) is then added dropwise, at such a race, that the temperature does not rise above 10° C. After the addition is complete the reaction mixture is stirred for a further 30 mins. The reaction mixture is cooled to 5° C. and Conc. hydrochloric acid (0.5 Mol) is gradually added, resulting in the immediate precipitation of a white solid, this slurry is stirred for a further 30 mins. The white solid is then separated by filtration and typically washed with ice water and diethyl ether. In the case of N-hexadecanoyl-2-aminoisobutyric acid, unwanted palmitic acid by-produce is separated by soxhlet extraction (diethyl ether, 7 hrs).

Azlactonisation of N-acylamino Acids-General Procedure

A suitable round bottom flask equipped with stirring bar and drying tube is charged with the desired N-acyl amino acid (1mol), dicyclohexylcarbodiimide [DCC] (1 mol) and THF (500ml). The reaction mixture is stirred at room temperature until FTIR shows no further reaction. The reaction mixture is filtered, the residues being washed with THF. The combined THF solutions are reduced to give crude azlactone which is either purified from n-hexane (2aryl azlactones) or distilled under reduced pressure (2-alkyl azlactones).

i) N-Benzoyl Glycine
Yield 75%,
1-NMR (CDCl,)d7.80(1H, bt, NH), 7.3(2H, d, Ph-HO6.9 (3H, m, Ph-H), 3.49 (2H,d,$CH_2$).

ii) N-Benzoyl Phenylalanine
Yield 50%.
1-H NMR ($CDCl_3$) d7.72–7.15 (10H, m, Ph-H), 6.62 (1H, d, NH), 5.08 (1H, q, CH), 3.30 (2h, DQ, $CR_2$).

iii) N-Benzoyl Alanine
Yield 61%
1H NMR ($CDCl_3$) d7.58 (1H, bd, NH), 7.32 (2H, d, Ph-H), 7.00–6.80 (3H, m, Ph-H), 4.10 (1H, m, CH), 0.92 (3H, d, $CH_3$).

iv) N-Benzoyl Methylalenine
Yield 54%
1-H NMR ($CDCl_3$) d7.60–7.10 (5H, m, Ph-H), 1.42 (6H, S, 2x$CH_3$), v) Glycine Azlactone
Yield 47%
I.R. (neat)n/$cm^{-1}$1820 (C=O), 1645 (C=N), vi) phenylalanine Azlactone
Yield 53%
I.R. (neat)n/$cm^{-1}$1820 (C=O), 1645 (C=N).
1-HNMR ($CDCl_3$) d7.97–7.10 (10H, m, Ph-H), 4.70 (1H, dd, CH), 3.40–3.10 (2H, m $CH_2$)

vii) Alanine Azlactone
Yield 43%
I.R. (neat)n/cm$^{-1}$1820 (C=O), 1650 (C=N).
1-HNMR (CDCl$_3$) d8.00 (2H, d, Ph-H), 7.60–7.35 (3H, m, Ph-H), 4.45 (1H, q, CH), 1.59 (3H, d, CH$_2$).

viii) Methylalanine Azlactone
Yield 97%
I.R. (neat)n/cm$^{-1}$1825 (C=O), 1655 (C=N).
1HNMR (CDCl$_3$) d8.00 (2H, m, Ph-H), 7.60–7.40 (3H, m Ph-H), 1.55 (6H, S, 2xCH$_3$).

ix) Pentadecyl Azlactone
Yield 60%
The 1-H NMR and 1R were consistent with the expected structure and GC showed it to be >99% pure.

Other classes of compound which deliver the desired benefits of hydrophobic modification leading to reversible styling and/or conditioning are:

Dialkyl disulphides

These contain the same disulphide linkage present in a keratin fibre. Thioglycollate reduction of hair followed by treatment with a 'fatty' dialkyldisulphide results in the reformation of disulphide linkages formed between keratin fibre and active.

The main benefit from this approach is that the bond attaching the hydrophobic alkyl group to the hair protein is via a hydrolytically stable disulphide bond.

By the use of the diestar of cystine the leaving group is an ester of cysteine which has little odour. By using cystine as the reactive electrophilic group the resulting linkage between protein and alkyl group is also cystine. The chemistry of the alkylation protocol is therefore directly analagous with the natural chemistry found within the fibre.

Thiosulphonates

Thiosulphonates can be readily synthesised via the condensation of a sulphonyl bromide (typically para-toluene sulphonylbromide) with an alkyl/aryl sulphide. This class of compound is reported in the literature to readily undergo reaction with suitable anions at the thio-sulphur atom releasing a sulphinic leaving group. This group is a much better leaving group than RS and hence the thiosulphonates are more reactive with the fibre than the dialkyldisulphides.

Thiuramdisulphides

This class of compound is the fully sulphonated analogue of dialkancylperoxides. The reactive chemistry of these materials is less well documented, it is reasonable to suggest that reactions with nucleophiles can take place via two different pathways. Both pathways give potentially attractive results since the by-products are believed to be significantly safer than ordinary sulphides.

Vinylsulphones

The Chemistry of vinylsulphones with respect to attack by nucleophiles is analogous to that of $\alpha,\beta$-unsaturated ketones in that they can undergo a 1,4- type Michael addition without releasing any undesirable by-products.

Vinyl Sulphoximines

These work in a similar way to vinylsulphones. The N-tosyl sulphoximine group is significantly more electron withdrawing than the phenyl sulphone and therefore the vinyl groups will be more susceptible towards nucleophilic attack. N-substituents can be used to alter the electrophilic potential of the vinyl group.

Masked Isocyanates can also be used.

The invention will now be described by way of example only and with reference to the following non-limiting examples.

Hair Switch Preparation

Ten hair fibres each of length greater than 18 cm were taken from a bundle of Yugo red tie hair. The fibres were bundled together length-wise side by side, watted with water to make handling easier, and a knot tied at just greater than 10 mm from the root and of the fibres. The knot was then secured in tacky adhesive against a flat horizontal surface and another knot was tied in that hair at precisely 150 mm from that first knot using an opened up paper clip to guide the knot into place. The free ands of the knotted bundle were then trimmed to precisely 10 mm from the knots. Quick setting glue (one drop) was carefully applied to the knots and along the lengths of the free hair taking care for it not to spread onto the 15 cm length of hair between the two knots.

EXAMPLE 1

Azlactone Treatment on the Curler

Five groups of four, 10 fibre, switches were prepared and wound onto a curler. Following the individual treatment, described below, the switches were removed from the curlers, suspanded (rt, 50%RH) and their initial lengths ($L_0$) measured immediately. The curl lengths were remeasured after 24h ($L_{24}$). The switches were then soaked in distilled water for 5 min at rt, dried on tissue paper and rehung—the initial lengths ($L_{water}$) were noted immediately. The curl lengths were remeasured after 24 h, The switches were set straight (ands temporarily stuck down) by soaking in 30% aqueous propanol for 15 min, dried with tissue paper and rehung. The lengths of the straightened switches were measured ($L_{straight}$). After 24h the switches were reset on a curler in the opposite direction to that of the initial set and soaked in 30% aqueous propanol for 1 h. Following drying and suspension the values for $L_0$ and $L_{24}$ were recorded as before. The switches were then reset a second time by winding them onto a curler in the original direction (i.e. as for the first set) and soaking in 30% aqueous propanol. $L_n$ and $L_{24}$ were noted as before.

Treatments

1A-Blank 4 switches were soaked in 30% aqueous propanol for one hour after which they were removed and dried (these switches were then aquilibrated at rt at 50%RH for a further 30 min).

1B-Thioglycollate 4 switches were treated with ammonium thioglycollate solution (15%, pH9.3) for 40 min at RT after which they were rinsed with distilled water and dried.

1C-Azlactone 4 switches were soaked in a solution of benzyl phenyl azlactone (0.067 M, pH 3.6 in 70% aqueous propanol) for 2h at rt. The switches were rinsed with distilled water and dried.

1D-Thioglycollate/Azlactone 4 switches were treated with ammonium thioglycollate solution (15% pH 9.3) for 40 min after which they were rinsed with distilled water. The reduced switches were then transferred to a solution of phenyl alanine azlactone (0.067 M, pH 3.6 in 70% aqueous propanol) and soaked for 2 h at rt. Following treatment with azlactone the switches were rinsed with distilled water and dried as above.

1E-Thioglycollate/Hydrogen Peroxide 4 switches were treated with ammonium thioglycollate solution (15%, pH 9.3) for 40 min after which they were rinsed with distilled water and transferred to a solution of hydrogen peroxide (10%) and soaked for 30 min. The switches were rinsed with distilled water and dried.

TABLE 1a

| Treatment | Curl Length L (Percentage Curl Retention CR)* Initial Set | | |
|---|---|---|---|
| | $L_o$ | $L_{24}$ $(CR_{24})$ | $L_{water}$ $(CR_{water})$ |
| 30% aqueous propanol 1A | 7.6 ± 0.2 | 11.5 ± 0.8 (48.6 ± 9.2) | 13.3 ± 0.6 (23.4 ± 8.2) |
| 1) 15% Ammonium thioglycollate 1D 2) 0.67M Azlactone | 6.3 ± 0.2 | 6.5 ± 0.3 (97.5 ± 3.1) | 7.7 ± 0.4 (83.9 ± 3.4) |
| Azlactone 1C | 7.9 ± 0.2 | 11.8 ± 44.7 (44.7 ± 3.1) | 14.1 ± 0.2 (12.2 ± 2.7) |
| 1) 15% Ammonium thioglycollate 1E 2) $H_2O_2$ | 6.4 ± 0.1 | 6.5 ± 98.6 (98.6 ± 1.1) | 9.1 ± 0.5 (66.4 ± 2.4) |
| 15% Ammonium thioglycollate 1B | 6.5 ± 0.1 | 6.7 ± 0.1 (97.3 ± 0.6) | 13.6 ± 0.5 (16.9 ± 5.6) |

*Percentage Curl Retention $CR = \dfrac{L^{dp} - L_t}{L^{dp} - L_0}$, where $L^{mn}$ = Switch Length (15.0 cm)
$L_o$ = Initial Curl Length
$L_t$ = Curl Length at time t

TABLE 1b

| Treatment | Curl Length/L (Percentage Curl Retention CR 1st Reset | | | | |
|---|---|---|---|---|---|
| | $L_{24}$ $(CR_{24})$ | $L_{straight}$ | $L_o$ | $L_{24}$ $(CR_{24})$ | $L_{water}$ $(CR_{water})$ |
| 30% aqueous propanol 1A | 13.4 ± 0.5 (21.8 ± 7.1) | 13.7 ± 0.9 (19.8 ± 9.4) | 7.9 ± 0.4 | 10.5 ± 0.7 (63.4 ± 8.5) | 13.9 ± 0.5 (15.5 ± 8.5) |
| 1)15% Ammonium thioglycollate 1 D 2)0.67 M Azlactone | 7.7 ± 0.4 (84.1 ± 4.4) | 13.3 ± 0.5 (19.4 ± 4.6) | 6.2 ± 0.1 | 6.2 ± 0.2 (99.2 ± 0.9) | 8.1 ± 0.3 (77.7 ± 2.6) |
| Azlactone 1 C | 14.2 ± 0.3 (10.8 ± 3.3) | 14.3 ± 0.3 (9.8 ± 3.5) | 7.9 ± 0.2 | 10.5 ± 0.4 (63.6 ± 4.9) | 13.8 ± 0.8 (17.6 ± 11.6) |
| 1)15% Ammonium thioglycollate 1 E 2)$H_2O_2$ | 8.3 ± 0.6 (78.2 ± 6.9) | 12.9 ± 0.3 (24.5 ± 3.6) | 6.2 ± 0.2 | 6.3 ± 0.2 (98.9 ± 1.0) | 9.3 ± 0.7 (64.7 ± 9.2) |
| 15% Ammonium thioglycollate 1 B | 13.6 ± 0.5 (16.9 ± 5.6) | 14.6 ± 0.1 (5.1 ± 1.5) | 6.5 ± 0.1 | 6.7 ± 0.2 (97.6 ± 1.2) | 12.6 ± 0.3 (28.2 ± 3.6) |

TABLE 1c

| Treatment | Curl Length/L (Percentage Curl Retention CR) 2nd Reset | | |
|---|---|---|---|
| | $L_o$ | $L_{24}$ | $L_{water}$ |
| 30% aqueous propanol 1A | 8.0 ± 0.3 | 10.8 ± 0.3 (60.5 ± 2.9) | 14.0 ± 0.4 (14.3 ± 5.7) |
| 1)15% Ammonium thioglycollate 1 D 2)0.67 M Azlactone | 6.1 ± 0.2 | 6.3 ± 0.2 (98.7 ± 1.3) | 8.4 ± 0.5 (74.4 ± 5.6) |
| Azlactone 1 C | — | — | — |
| 1)15% Ammonium thioglycollate 1 E 2)$H_2O_2$ | 6.4 ± 0.1 | 6.4 ± 0.1 (99.6 ± 0.6) | 10.1 ± 0.3 (57.3 ± 3.6) |
| 15% Ammonium thioglycollate 1 B | 6.6 ± 0.3 | 6.7 ± 0.3 (98.2 ± 1.3) | 12.7 ± 0.2 (27.9 ± 2.7) |

RESULTS AND DISCUSSION

The results are shown in Table 1, It can clearly be seen that the treatments with thioglycollate, thioglycollate/ azlactone and thioglycollate/hydrogen peroxide give a superior set in comparison with a water wave and azlactone by itself and that this set displays no significant loss of curl retention over 24 h. On soaking the fibres in water, complete loss of set is observed with the thioglycollate treated switches. However, excellent set retention (both initial and after 24 h) was observed for the fibres treated with thioglycollate/azlactone. The set retention for the permanently waved hair was comparable. All five groups of switches were able to be set straight by soaking in aqueous propanol.

On resetting the switches, the initial set and set retention after 24 h for all 5 groups of switches was similar to the first step. On soaking in water the curl retention was again similar to that following the first soak for all the groups apart from the permed hair which lost considerable curl definition. This is perhaps not unexpected since the curl in the first set would primarily be held by newly formed disulphide bonds while the second set would be held as a result of internal hydrogen bonds and salt linkages. On soaking in water these polar interactions will be broken allowing the internal disulphide bonds to pull the hair back towards its original set. The result is that although the curl length retention is quantitatively reasonable, visually the curl is of extremely poor quality.

The observation for the second reset mirrors that of the first with the curl quality, definition and retention remaining high for the reduced/azlactone treated hair and the corresponding parameters deteriorating for the permed hair.

This example was repeated at the lower azlactone concentration of and 0,03M, and the results obtained were comparable with the above examples.

CONCLUSION

Hair which is reduced with ammonium thioglycollate followed by treatment with aryl azlactones displays excellent initial set and set retention comparable with that shown by permanent waved hair. The azlactone treated hair also displays excellent robustness of set when soaked in water which is superior to that of permanent waved hair. Unlike permanent waved hair, the azlactone treated hair can be restyled at least twice by resetting the hair and soaking in aqueous propanol. The subsequent curl displays excellent curl retention both before and after soaking in water. The observed set retention and resistance to water induced disruption of the set is due to the introduction of hydrophobic groups (phenyl/benzyl) to reactive nucleophilic sites on the hair fibre. Thioglycollate treated hair displays excellent initial set and set retention comparable with thioglycollate/ azlactone and thioglycollate/hydrogen peroxide treated hair. But, this set is not resistant to water.

EXAMPLE 2

Treatment off the Curler

Resetting Cycle

For each of the treatments described below the resetting cycle is as follows:
i) Soak in water for 5 minutes, reset as described for Example 1 onto the curlers, dry at 50° C., cool at 21° C./50% RH, remove from the curlers and measure length of switches after 24 h.
ii) Soak in water for 5 min, suspand against graph paper, equilibrate for 24 h and measure lengths.
iii) Set straight by soaking in water for 5 min, fix a fully extanded conformation, dry at 50° C. for 30 min, cool at 21° C./50% RH for 30 min and measure length.
i) Repeat of steps i) and ii).
v) Repeat of step i) except that switches are soaked in 70% aqueous n-propanol instead of water.
v) Repeat of step ii).
vi) Finally immeres the switches in 70% aqueous n-propanol for 10 min, equilibrate at 21° C./50% RH for 24 h and measure again.

2A-Thioglycollate Alone

The switches as described above (four replicates) were each soaked loose in 15% ammonium thioglycollate solution (15 ml) at pH 9.3 for 40 min at ambient temperature. The switches were then rinsed under 30° C. tap water for 2 min, and put through the setting and percentage CR evaluation protocol, as described below:

Setting and Percentage Curl Retention (CR) Evaluation Protocol

Each switch was then secured by its 1 cm root and length of hair with a 2 mm diameter/2 mm length sleeve to the and of a curler moulded into a spiral shape with a diameter of 10 mm and a pitch of 7.5 mm and cut down to 182 mm in length prior to use. The free end of hair of the switches was then wound along the spiral of the curler by hand and the 1 cm tip-and diameter/2 mm length sleeve.

The roller-mounted switches were then left to dry in a circulatory oven at 50° C. for 30 min and allowed to cool to 21° C. at 50% RH for a further 30 min. The switches were then removed from the rollers, suspanded against graph paper and their lengths immediately measured. The switches were left handing for a further 24 h at 21° C., 50% RH and their lengths were again measured.

2B-Thioglycollate+Hydrogen Peroxide Oxidation Step

The previous experiment was repeated exactly using fresh switches except that after the hair was reduced with the thioglycollate solution and rinsed under 30° C. tap water the switches were soaked loose in hydrogen peroxide (2.4%, pH 3 with phosphoric acid ) (15 ml). The switches were then put through the setting and percentage CR evaluation protocol.

2C-Thioglycollate+Alkyl Azlactone

The first experiment was repeated exactly using fresh switches except that this time, after the reduction and rinsing step, the hair was soaked in a solution comprising hexyl azlactone (33%), n-propanol (50%) and pH 9 buffer (17%), (treated at 10:1 solution to hair ratio) solution for 1 h at ambient temperature. The switches were then rinsed in 70% aqueous n-propanol for 2 min with agitation, and put through the setting and percentage CR evaluation protocol.

2D-Alkyl Azlactone Alone

Fresh switches were soaked in water at ambient temperature for 15 min and then soaked in solution comprising hexyl azlactone (33%), n-propanol (50%) and pH buffer (17%) for 1 h at ambient temperature. The switches were then rinsed in 70% aqueous n-propanol for 2 min with agitation, and put through the setting and percentage CR evaluation protocol.

2E-Water Wave Control

Four replicate switches were soaked in water for 15 min at ambient temperature and set onto the rollers as before. They were dried and equilibrated as before and put through the setting and CR evaluation protocol.

TABLE 2a

| Entry Columns | Treatment | Initial CL[a] (cm) 1 | % CR[b] after 24 h 2 | % CR after 5 min in water + 24 h 3 | CL after reset (cm) 4 | % CR after 24 h 5 |
|---|---|---|---|---|---|---|
| 2A | TG[d] alone | 6.8 ± 0.1 | 95 ± 1 | 5 ± 1 | 6.6 ± 0.1 | 96 ± 1 |
| 2B | TG ± H$_2$O$_2$ | 7.1 ± 0.2 | 93 | 24 ± 9 | 6.6 | 95 ± 1 |
| 2C | TG + Alkyl Azlactone | 6.4 ± 0.1 | 94 ± 1 | 55 ± 3 | 6.4 ± 0.1 | 97 ± 1 |
| 2D | Alkyl Azlactone alone | 8.7 ± 0.3 | 36 ± 5 | 15 ± 5 | 7.9 ± 0.1 | 66 ± 3 |
| 2E | Water alone | 8.5 ± 0.4 | 58 ± 3 | 13 ± 2 | 8.1 ± 0.1 | 66 ± 1 |

[a] = CL is curl length
[b] = CR is curl retention
[c] = PrOH is aqueous propanol
[d] = TG is thioglycollate TABLE 2b

| Entry Columns | Treatment | % CR after 5 min in water + 24 h 6 | L$_{straight}$* 7 | L$_o$(cm) 8 | % CR after 24 h 9 | % CR after 5 min in water + 24 h/cm 10 |
|---|---|---|---|---|---|---|
| 2A | TC[d] alone | 6 ± 1 | 14.8 ± 0.1 | 6.7 ± 0.1 | 93 ± 1 | 7 ± 3 |
| 2B | TG + H$_2$O$_2$ | 21 ± 10 | 12.9 ± 0.8 | 6.6 ± 0.1 | 93 ± 1 | 24 ± 6 |

TABLE 2b-continued

| Entry Columns | Treatment | % CR after 5 min in water + 24 h 6 | $L_{straight}$* 7 | $L_o$(cm) 8 | % CR after 24 h 9 | % CR after 5 min in water + 24 h/cm 10 |
|---|---|---|---|---|---|---|
| 2C | TG + Alkyl Azlactone | 67 ± 3 | 14.3 ± 0.3 | 6.6 ± 0.2 | 93 ± 1 | 34 ± 2 |
| 2D | Alkyl Azlactone alone | 13 ± 5 | 14.0 ± 0.4 | 7.7 ± 0.1 | 64 ± 3 | 11 ± 4 |
| 2E | Water alone | 10 ± 3 | 14.3 ± 0.1 | 7.8 ± 0.1 | 59 ± 1 | 11 ± 3 |

*$L_{straight}$ = length after set straight and then soaked in water

TABLE 2c

| Entry Columns | Treatment | Length after 10 min in PrOH$^c$ + 24 h/cm 11 | % CR after 24 h 12 | % CR after 5 min in water + 24 h/cm 13 | % CR after 10 min in PrOH 14 |
|---|---|---|---|---|---|
| 2A | TG$^d$ alone | 6.9 ± 0.1 | 89 ± 2 | 4 ± 1 | No change |
| 2B | TG + H$_2$O$_2$ | 6.9 ± 0.1 | 93 ± 1 | 27 ± 6 | No change |
| 2C | TG + Alkyl Azlactone | 6.4 ± 0.1 | 98 ± 1 | 54 ± 2 | 24 ± 5 |
| 2D | Alkyl Azlactone alone | 7.9 ± 0.1 | 70 ± 3 | 11 ± 4 | No change |
| 2E | Water alone | 8.1 ± 0.1 | 67 ± 2 | 11 ± 3 | No change |

RESULTS AND DISCUSSION

The results of the hair setting studies are shown in Table 2. From the first, column in the table it can be seen that the thioglycollate/alkyl azlactone treatment gave a significantly superior initial set (smallest initial curl length) than any of the other treatments. After 24 hr at 50% RH curl retention of the thioglycollate alkyl/azlactone treated switch was significantly greater than the water wave.

It is clear that alkyl azlactone does not confer significant set retention to hair when used on its own without a pre-reduction step on the hair. However, in does react with surface nucleophilic groups to give a conditioning benefit.

In column 3 of the table, it can be seen that the set imparted by the treatment 2C is much more resilient to degradation by water then the set imparted by any of the other treatments. This indicates that the residual set after the thioglycolate/ alkyl azlactone treatment was 'hydrophobic', and the curl definition is wall retained.

The hair was reset onto the curlers. It can be seen that the curl lengths immediately after removing the switches from the curlers (column 4) are comparable to, or in some cases, better than before.

After immersing the curls in water the curl retention value for the thioglycollate/hexyl azlactone treatment was vastly superior to any of the other treatments. This shows that the 'hydrophobic' setting effect still remained after the resetting process.

The results of setting the hair straight and determining the resiliency of the straight set to water are shown in column 7. It can be seen that the thioglycollate treatment and the thioglycollate/hexyl azlactone treatment retain the straight configuration very well. The permed switches on the other hand, adopted the configuration they were originally in whilst being treated. These results indicate that the switches treated with thioglycollate and thioglycollate/hexyl azlactone have the ability to the reversibly set.

The resettability of hair with aqueous propanol was tested and the results are given in column 11. Styling with propanol enhances the set retention of the hair by disrupting the hydrophobic bonds and allowing them to be set in a greater 'set retaining'configuration on evaporation of the propanol from the fibre than that obtained with water alone.

Finally, the results shown in column 14 provided a further demonstration that hydrophobic bonds were indeed responsible for maintaining the set with the thioglycollate/hexyl azlactone treatment alone. Here, immersion of the hair samples in aqueous propanol resulted in an appreciable reduction in the set retention value compared with the previous value in column 13.

It is worth emphasizing that the impressive stylability and set retention results obtained with the thioglycollate/alkyl azlactone treatment in these experiments were obtained without the need for the hair to be mounted on curlers/rollers whilst the treatment was in contact with the hair. Not only does this provide convincing evidence that the hydrophobic setting effect really is in operation after use of alkyl azlactone, but it also indicates that the treatment could be more convenient to use in vivo than conventional perming where rollers are needed during the application of both the reducing and oxidising lotions.

We also studied the settability/resettability of alkyl azlactone-treated reduced hair compared to reduced hair treated with N-benzyl maleimide

COMPARATIVE EXAMPLE A

Thioglycollate+N-Benzyl Maleimide Under Non-Wolfram Conditions

The first treatment was repeated using fresh switches except that after the reduction and rinsing step the hair was soaked in a solution comprising N-Benzyl Maleimide (33%), n-propanol (50%) and pH9 buffer (17%), at a solution: hair ratio of 10:1 for 1 hr at ambient temperature.

This procedure was also conducted at pH 7.

COMPARATIVE EXAMPLE B

Thioglycollate+N-Benzyl Maleimide Under Condition Similar to Wolfram's

To compare treatments according to the invention with conditions found in the prior art the first treatment was repeated using fresh switches except that after the reduction and rinsing step the hair was soaked in a solution of N-Benzyl Maleimide (0.016M, in propanol (20%), pH 7 buffer (80%) mix), (15ml) for 2 hrs at 35° C. The switches were rinsed with 50% aqueous propanol for 5 min and subjected to the setting cycle stages as with the previous treatments.

The results are shown in Table 3:

TABLE 3

| Example | Treatment | % CR (95% confidence) |
|---|---|---|
| Comparative Example A | Thioglycollate/ benzyl maleimide pH7 | 29.5 ± 4.1 |
| | Thioglycollate/ benzyl maleimide pH9 | 29.7 ± 4.3 |
| Comparative Example B | Thioclygollate/ benzyl maleimide (Wolfram's conditions) | 46.5 ± 4.8 |

RESULTS AND DISCUSSION

When N-benzyl-maleimide was applied under the same conditions as pentadecyl azlactone at either pH 7.0 or 9.2 it was no better than thioglycollate alone.

Wolfram found that treatment of reduced hair with N-benzyl maleimide gave enhanced settability and high set retention through the hydrophobic bonding mechanism. However, we found no benefit from this material when applied under the same conditions as pentadecylazlactone. However, we did find a benefit when N-benzyl maleimide was applied under conditions similar to Wolfram's. These results suggest that the azlactone functionality is superior to the maleimide functionality for imparting hydrophobic setting to hair.

When pentadecyl azlactone was applied to hair at pH 7 instead of pH 9 it gave a comparable effect to application at pH 9, indicating that the high pH of 9 is not necessary for effective acylation of hair thiol groups by azlactones.

It should be pointed out that maleimides are known skin sensitisers which has precluded their development into commercial hair products.

CONCLUSIONS

It has bean demonstrated that hair treated with thioglycollate/alkyl azlactone, without mechanical deformation (curler/roller) whilst the treatment was in contact with the hair, displayed the following properties in vitro:

Stylability and set retention which were superior in resilience to water degradation than the stylability and set retention properties obtained with thioglycollate alone or thioglycollate with subsequent oxidation. The ability to be reset with water and heat to the same degree of efficiency as obtained in the initial setting process and reversible styling, whereby the hair could be returned from its curly set to a water-resilient straight configuration with water and heat then restyled back into the curly set with the same set retention ability as the original one with aqueous propanol.

These results indicate that, under the conditions used, sufficient hexyl azlactone can acylate free thiol groups generated in hair by thioglycollate to give a set which is 'hydrophobic' in nature.

It has bean shown that the azlactone functionality, as present in alkyl azlactone and aryl azlactone, is useful for acylating thiol groups of thioglycollate-reduced hair fibres to confer 'hydrophobic' settability resettability to the hair.

EXAMPLE 3

Test of Pentadecyl Azlactone to Give 'Permanent'Conditioning to Hair

Six 25.4 cm/7g hair switches were prepared from Yugo hair. The switches were degreased by soaking in 5% SLES 2EC overnight, rinsed thoroughly and dried. They were than soaked in distilled water for 10 min before applying 1 ml of the following mixture to each of three of the switches; pentadecyl azlactone (33%)/n-propanol (50%) pH 9 buffer (17%). The other three switches were treated with 1 ml/switch of the control mixture: n-propanol (75%)/pH 9 buffer (25%). The mixtures were spread evenly along the switches, the switches put in a sealed container and left for 1 hr at ambient temperature. The switches were then immersed in stirred 70% aqueous n-propanol (1.51) for 1hr, dried at 50° C. for 30 min, combed, and panel tested for smoothness and ease of combability according to standard tests. The switches were then soaked in stirred n-propanol (1.51) for a further 1 hr, rinsed with tap water, washed with SLES 2EC, dried and again panel tested for smoothness and ease of combability.

The results are given on Table 4:

TABLE 4

| | Voting Split for Switches | | | |
|---|---|---|---|---|
| | After 1st Propanol Rinse | | After 2nd Propanol rinse + Shampoo | |
| Attribute | Test | Control | Test | Control |
| Smoothness | 45 | 27 | 50 | 22 |
| Ease of Comb | 53 | 17 | 47 | 25 |

The conditioning benefits given by the pentadecyl azlactone can be clearly seen.

EXAMPLE 4

Thioglycollate+Alkyl Azlactone Treatment of African Hair

Thioglycollate+pentadecyl azlactone treatment of tightly curled hair such as Negro hair gives it the ability to be set into any desired configuration (e.g. straight or wavy) with the set having a high degree of water stability. Not only does this provide a potentially less damaging method for straightening Negro hair than the use of caustic treatments, it also is a potentially useful method for cutting out a step in Negro hair (chemical treatment) styling, viz; caustic treatment is used principally to straighten negro hair and it a degree of waviness is required in the straightened hair it is then rolled onto curling rods and treated further with thioglycollate+ oxidising agent. The thioglycollate +pentadecyl azlactone treatment on the other hand, enables the straightened hair to be set wavy without the need for further chemical treatment.

EXAMPLES 5 to 8

Comparison of Alkyl and Aryl Azlactones

Hair switches were reduced with ammonium thioglycollate, rinsed with water and treated with azlactone at pH 9.2. The fibres were then set using 70% aqueous propanol. Results are given in Table 5.

TABLE 5

|   | TEST COMPOUND | CURL RETENTION (FIRST SET) |
|---|---|---|
| 5. | 2-Benzyl-4,4'-Dimethyl Azlactone | 13.9 ± 3.8 |
| 6. | 2-Phenyl-4,4'-Dimethyl Azlactone | 20.1 ± 2.6 |
| 7. | 2 Benzyl-4-Phenyl | 27.3 ± 1.4 |
| 8. | 2-Pentadecyl-4,4' Dimethyl Azlactone | 76.1 ± 1.5 |

It can be seen that the set retention from the alkyl azlactone is far superior to that obtained from any of the aryl azlactones.

EXAMPLES 9 to 13

Effect of Alkyl Chain Length (for Azlactone) on Curl Drop Out

Hair switches were treated as described for Examples 5 to 8. Results are given in Table 6:

TABLE 6

| Example | Alkyl Chain Length of the Azlactone | % CR (95% confidence) |
|---|---|---|
| 9 | 6 | 83.0 ± 5.0 |
| 10 | 9 | 80.3 ± 9.8 |
| 11 | 11 | 77.5 ± 1.5 |
| 12 | 15 | 78.2 ± 5.5 |
| 13 | 17 | 82.3 ± 5.4 |

It can be seen that altering the alkyl chain length of the azlactone from $C_6$ through to $C_{17}$ has no effect on styling efficacy.

ESXAMPLE 14 and 15

Comparison of Alkyl and Aryl Thiosulphonates

Hair switches were reduced with ammonium thioglycollate, rinsed with water and treated with thiosulphonate at pH 9.3.

The fibres were then set using 70% aqueous propanol. Results are given in Table 7.

TABLE 7

| Example | Test Compound | % CR (95% confidence) |
|---|---|---|
| 14 | Dodecyl thiosulphonate | 64.6 ± 7.8 |
| 15 | Phenyl thiosulphonate | 35.6 ± 4.7 |

It can be seen that the set retention from the alkyl thiosulphonate is superior to that obtained from the aryl thiosulphonate.

We claim:

1. A hair styling and conditioning process comprising the steps of: contacting the hair with a compound having an electrophilic group and at least one hydrophobic group whereby the electrophilic group reacts with nucleophilic sites in and on the hair to give the hair a plurality of hydrophobic groups at a surface of the hair, in which the compound is an azlactone of formula:

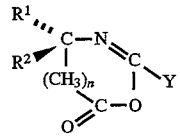

wherein $R^1$ and $R^2$ are the same or different and each is independantly selected from the group consisting of H and $C_{1-4}$ alkyl groups, and Y is selected from the group consisting of $C_{10-30}$ alkyl and $C_{10-30}$ alkenyl groups.

2. The process of claim 1 in which Y is $C_{11}-C_{16}$ alkyl.

3. The process of claim 1 in which the compound is pentadecyl azlactone.

4. The process of claim 1 in which the hair is contacted with a reducing agent before it is treated with the electrophilic group.

5. The process of claim 4 in which the reducing agent is thioglycollate.

6. The process of claim 1 in which styled hair is restyled by contacting the styled hair a liquid containing hydrophillic and hydrophobic groups, then setting the hair.

7. The process of claim 6 in which the liquid contains alcohol.

* * * * *